US008663950B2

(12) United States Patent
Chen et al.

(10) Patent No.: US 8,663,950 B2
(45) Date of Patent: Mar. 4, 2014

(54) PRODUCTION OF A MONOCLONAL ANTIBODY THERAPEUTIC AGAINST WEST NILE VIRUS IN PLANTS

(75) Inventors: Qiang Chen, Chandler, AZ (US); Huafang Lai, Chandler, AZ (US)

(73) Assignee: Arizona Board of Regents, Scottsdale, AZ (US)

( * ) Notice: Subject to any disclaimer, the term of this patent is extended or adjusted under 35 U.S.C. 154(b) by 0 days.

(21) Appl. No.: 13/521,431

(22) PCT Filed: Jan. 10, 2011

(86) PCT No.: PCT/US2011/020635
§ 371 (c)(1), (2), (4) Date: Jul. 10, 2012

(87) PCT Pub. No.: WO2011/085289
PCT Pub. Date: Jul. 14, 2011

(65) Prior Publication Data

US 2012/0329994 A1 Dec. 27, 2012

Related U.S. Application Data

(60) Provisional application No. 61/293,828, filed on Jan. 11, 2010.

(51) Int. Cl.

| | |
|---|---|
| ***C12P 21/02*** | (2006.01) |
| ***A61K 39/42*** | (2006.01) |
| ***C07K 1/14*** | (2006.01) |
| ***C07K 1/16*** | (2006.01) |
| ***C07K 1/18*** | (2006.01) |
| ***C07K 1/22*** | (2006.01) |
| ***C07K 1/36*** | (2006.01) |

(52) U.S. Cl.
USPC ....... 435/69.1; 435/414; 435/430; 424/133.1; 424/159.1; 530/387.3; 530/388.3; 530/412; 530/413; 530/416

(58) Field of Classification Search
None
See application file for complete search history.

(56) References Cited

U.S. PATENT DOCUMENTS

| | | | |
|---|---|---|---|
| 2002/0122798 | A1 | 9/2002 | Young |
| 2004/0001825 | A1 | 1/2004 | Govidan et al. |
| 2006/0165681 | A1 | 7/2006 | Ellis et al. |
| 2009/0041763 | A1 | 2/2009 | Kwon |
| 2009/0110632 | A1 | 4/2009 | Young et al. |
| 2009/0258011 | A1 | 10/2009 | Diamond et al. |

OTHER PUBLICATIONS

International Search Report and Written Opinion as mailed on Apr. 22, 2011 for International Application No. PCT/US2011/020635.

Huang et al. High-level rapid production of full-size monoclonal antibodies in plants by a single-vector DNA replicon system. Biotechnol Bioeng ePub Dec. 31, 2009 vol. 106 No. 1 pp. 9-17. Especially p. 11 left col. para 2, p. 12 left col. para 2, p. 12 right col. para 2-4, p. 13 right col. para 1.

Eriksson et al. MAb Contaminant Removal with a Multimodal Anion Exchanger. Bioprocess Int Feb. 2009 vol. 7 No. 2 pp. 52-56. Especially p. 53 center col. para 2, p. 55 table 3.

*Primary Examiner* — Louise Humphrey

(74) *Attorney, Agent, or Firm* — Quarles & Brady LLP; Gavin J. Milczarek-Desai

(57) ABSTRACT

The present invention describes the plant-based production of a therapeutic antibody against West Nile Virus.

11 Claims, 5 Drawing Sheets

Figure 3:
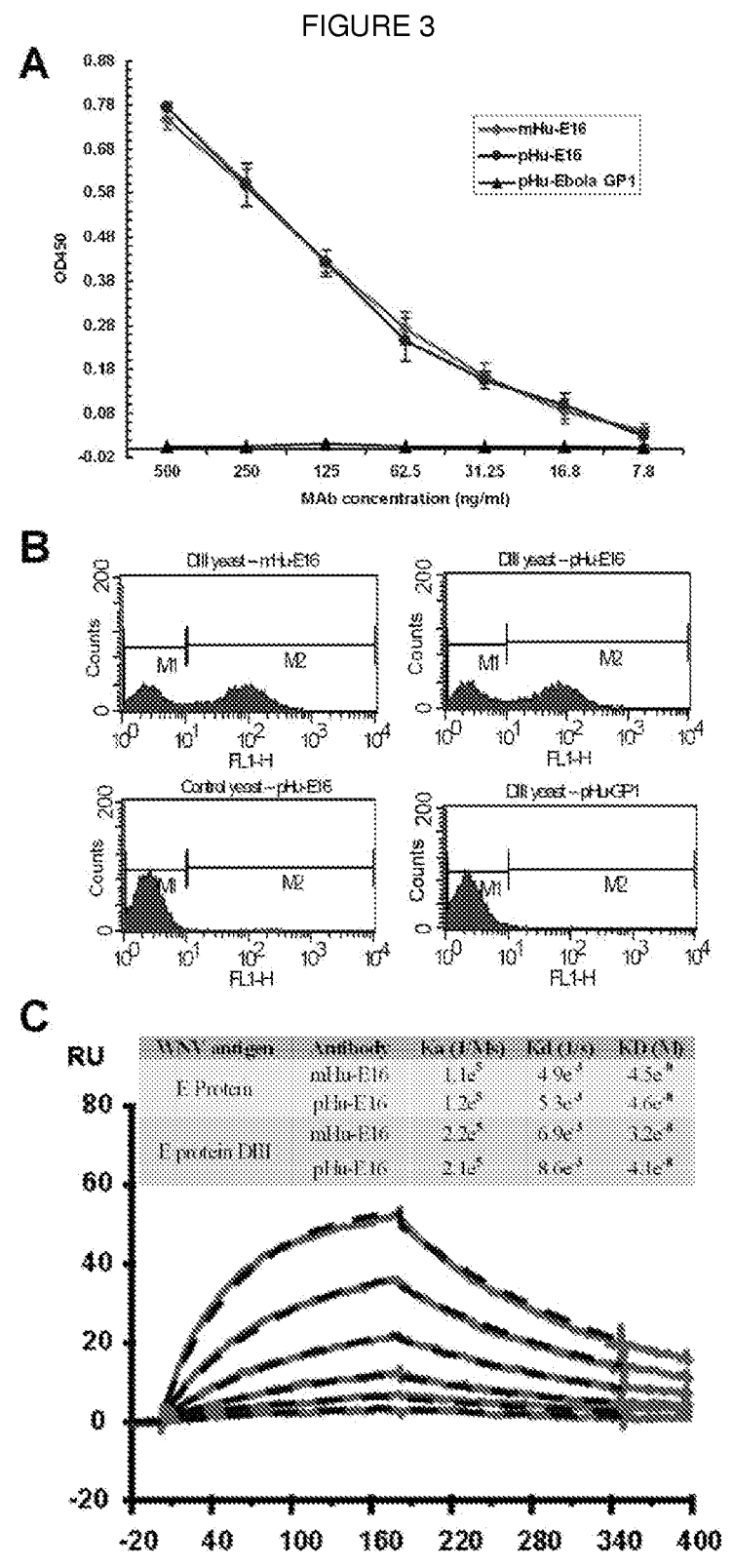

| WNV antigen | Antibody | ka (1/Ms) | kd (1/s) | KD (M) |
| --- | --- | --- | --- | --- |
| E Protein | mHu-E16 | $1.1e^5$ | $4.9e^3$ | $4.5e^8$ |
| | pHu-E16 | $1.2e^5$ | $5.3e^3$ | $4.6e^8$ |
| E protein DIII | mHu-E16 | $2.2e^5$ | $6.9e^3$ | $3.2e^8$ |
| | pHu-E16 | $2.1e^5$ | $8.6e^3$ | $4.1e^8$ |

SEQUENCE LISTING

```
<160> NUMBER OF SEQ ID NOS: 11

<210> SEQ ID NO 1
<211> LENGTH: 650
<212> TYPE: DNA
<213> ORGANISM: Artificial Sequence
<220> FEATURE:
<223> OTHER INFORMATION: Plant optimized new E16p Nucleic Acid
      sequence-HC variable region (EcoRI-intronless signal
      sequence-HC-HindIII)

<400> SEQUENCE: 1
```

```
gaattcacaa tgggatggtc ttgtatcatc cttttcttgg ttgcaacagc tactggtgtt     60

cattctcaag ttcaattggt gcagtcaggt gctgaggtga agaaaccagg tgcttcagtt    120

aaggtttctt gtaaggcttc tggttacaca ttcacagatt attggattga atgggtgaga    180

caagctcctg gtcagggtct tgagtggatg ggagatattc tttgtggaac tggaagaact    240

agatacaacg agaaacttaa ggctagagtt actatgactg ctgatacctc tacatctact    300

gcttacatgg aacttagatc tttgagatca gatgacactg ctgtgtacta ttgtgctagg    360

tcagcttctt atggagacta cgctgactat tggggacaag gtactactgt tactgtgtct    420

tctgcttcta ccaagggacc ttctgttttt ccacttgctc cttcttctaa gtctacttct    480

ggtggaactg ctgctttggg ttgtttggtg aaagattact ttcctgagcc agtgaccgtt    540

tcttggaact caggtgctct tacatctggt gttcatactt tcccagctgt tcttcaatct    600

tcaggacttt actcactttc ttctgttgtt accgttcctt cttcaagctt               650
```

```
<210> SEQ ID NO 2
<211> LENGTH: 449
<212> TYPE: PRT
<213> ORGANISM: Artificial Sequence
<220> FEATURE:
<223> OTHER INFORMATION: Plant optimized new E16p Amino Acid sequence-HC
      variable region (EcoRI-intronless signal sequence-HC-HindIII)

<400> SEQUENCE: 2

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Trp Ile Glu Trp Val Arg Gln Ala Pro Gly Gln Gly Leu Glu Trp Met
        35                  40                  45

Gly Asp Ile Leu Cys Gly Thr Gly Arg Thr Arg Tyr Asn Glu Lys Leu
    50                  55                  60

Lys Ala Arg Val Thr Met Thr Ala Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Ser Ala Ser Tyr Gly Asp Tyr Ala Asp Tyr Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
```

```
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys


<210> SEQ ID NO 3
<211> LENGTH: 449
<212> TYPE: PRT
<213> ORGANISM: Artificial Sequence
<220> FEATURE:
<223> OTHER INFORMATION: VH sequence of E16p Amino Acid sequence-heavy
      chain

<400> SEQUENCE: 3

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Trp Ile Glu Trp Val Arg Gln Ala Pro Gly Gln Gly Leu Glu Trp Met
        35                  40                  45

Gly Asp Ile Leu Cys Gly Thr Gly Arg Thr Arg Tyr Asn Glu Lys Leu
    50                  55                  60

Lys Ala Arg Val Thr Met Thr Ala Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Ser Ala Ser Tyr Gly Asp Tyr Ala Asp Tyr Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160
```

```
Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys
```

<210> SEQ ID NO 4
<211> LENGTH: 1615
<212> TYPE: DNA
<213> ORGANISM: Artificial Sequence
<220> FEATURE:
<223> OTHER INFORMATION: Total optimized heavy chain sequence (variable and constant region together)

<400> SEQUENCE: 4

```
gaattcacaa tgggatggtc ttgtatcatc cttttcttgg ttgcaacagc tactggtgtt      60

cattctcaag ttcaattggt gcagtcaggt gctgaggtga agaaaccagg tgcttcagtt     120

aaggtttctt gtaaggcttc tggttacaca ttcacagatt attggattga atgggtgaga     180

caagctcctg gtcagggtct tgagtggatg ggagatattc tttgtggaac tggaagaact     240

agatacaacg agaaacttaa ggctagagtt actatgactg ctgatacctc tacatctact     300

gcttacatgg aacttagatc tttgagatca gatgacactg ctgtgtacta ttgtgctagg     360
```

```
tcagcttctt atggagacta cgctgactat tggggacaag gtactactgt tactgtgtct    420

tctgcttcta ccaagggacc ttctgttttt ccacttgctc cttcttctaa gtctacttct    480

ggtggaactg ctgctttggg ttgtttggtg aaagattact ttcctgagcc agtgaccgtt    540

tcttggaact caggtgctct tacatctggt gttcatactt tcccagctgt tcttcaatct    600

tcaggacttt actcactttc ttctgttgtt accgttcctt cttcaagctt gggcactcag    660

acctacatct gcaatgtgaa tcacaaaccc agcaacacca aggttgacaa gaaagttgag    720

cccaagtctt gtgacaagac tcatacgtgt ccaccgtgcc cagcacctga acttcttgga    780

ggaccgtcag tcttcttgtt tcctccaaag cctaaggata ccttgatgat ctccaggact    840

cctgaagtca catgtgtagt tgtggatgtg agccatgaag atcctgaggt gaagttcaac    900

tggtatgtgg atggtgtgga agtgcacaat gccaagacaa agccgagaga ggaacagtac    960

aacagcacgt acagggttgt ctcagttctc actgttctcc atcaagattg gttgaatggc   1020

aaagagtaca agtgcaaggt ctccaacaaa gccctcccag cccccattga gaagaccatt   1080

tccaaagcga aagggcaacc ccgtgaacca caagtgtaca cacttcctcc atctcgcgat   1140

gaactgacca agaaccaggt cagcttgact tgcctggtga aaggcttcta tccctctgac   1200

atagctgtag agtgggagag caatgggcaa ccggagaaca actacaagac tacacctccc   1260

gttctcgatt ctgacggctc cttcttcctc tacagcaagc tcacagtgga caagagcagg   1320

tggcaacaag ggaatgtctt ctcatgctcc gtgatgcatg aggctcttca caatcactac   1380

acacagaaga gtctctcctt gtctccgggt aaatgaggat cctctagagt cgacctgcag   1440

ggtctcagct tggtcgtatc actggaacaa caaccgctga ggctgttgtc actctaccac   1500

caccataact acgtctacat aaccgacgcc taccccagtt tcatagtatt ttctggtttg   1560

attgtatgaa taatataaat aaaaaaaaaa aaaaaaaaaa aaaactagtg agctc        1615
```

```
<210> SEQ ID NO 5
<211> LENGTH: 468
<212> TYPE: PRT
<213> ORGANISM: Artificial Sequence
<220> FEATURE:
<223> OTHER INFORMATION: Translation of optimized heavy chain sequence

<400> SEQUENCE: 5

Met Gly Trp Ser Cys Ile Ile Leu Phe Leu Val Ala Thr Ala Thr Gly
1               5                   10                  15

Val His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Asp Tyr Trp Ile Glu Trp Val Arg Gln Ala Pro Gly Gln Gly Leu
    50                  55                  60

Glu Trp Met Gly Asp Ile Leu Cys Gly Thr Gly Arg Thr Arg Tyr Asn
65                  70                  75                  80

Glu Lys Leu Lys Ala Arg Val Thr Met Thr Ala Asp Thr Ser Thr Ser
                85                  90                  95

Thr Ala Tyr Met Glu Leu Arg Ser Leu Arg Ser Asp Asp Thr Ala Val
            100                 105                 110

Tyr Tyr Cys Ala Arg Ser Ala Ser Tyr Gly Asp Tyr Ala Asp Tyr Trp
        115                 120                 125

Gly Gln Gly Thr Thr Val Thr Val Ser Ser Ala Ser Thr Lys Gly Pro
    130                 135                 140

Ser Val Phe Pro Leu Ala Pro Ser Ser Lys Ser Thr Ser Gly Gly Thr
```

```
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Gln Thr Tyr Ile Cys Asn Val Asn
    210                 215                 220

His Lys Pro Ser Asn Thr Lys Val Asp Lys Lys Val Glu Pro Lys Ser
225                 230                 235                 240

Cys Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

His Glu Asp Pro Glu Val Lys Phe Asn Trp Tyr Val Asp Gly Val Glu
    290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
            340                 345                 350

Ile Glu Lys Thr Ile Ser Lys Ala Lys Gly Gln Pro Arg Glu Pro Gln
        355                 360                 365

Val Tyr Thr Leu Pro Pro Ser Arg Asp Glu Leu Thr Lys Asn Gln Val
    370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Lys Leu Thr
            420                 425                 430

Val Asp Lys Ser Arg Trp Gln Gln Gly Asn Val Phe Ser Cys Ser Val
        435                 440                 445

Met His Glu Ala Leu His Asn His Tyr Thr Gln Lys Ser Leu Ser Leu
    450                 455                 460

Ser Pro Gly Lys
465


<210> SEQ ID NO 6
<211> LENGTH: 702
<212> TYPE: DNA
<213> ORGANISM: Artificial Sequence
<220> FEATURE:
<223> OTHER INFORMATION: Nucleic acid for the optimized light chain
      sequence

<400> SEQUENCE: 6

atgggatggt cttgtatcat ccttttcttg gttgcaacag ctactggtgt tcattctgat      60

atcgttatga cacaatctcc agattctttg gctgtttctc ttggagagag ggctactatc     120

aattgcaagg cttctcaaga tgtttctact gctgttgctt ggtaccaaca gaaacctgga     180

cagccaccaa aacttcttat ctcttgggca tctactaggc acactggagt tccagataga     240
```

```
ttttctggat ctggatctgg aacagatttc actcttacta tctcatctct tcaagctgag    300

gatgttgcag tttattactg tcagcaacat tatacaactc cacttacttt cggacaagga    360

actaagttgg agatcaaaag aactgttgct gcaccatctg ttttcatctt ccctccatct    420

gatgagcagt tgaaatctgg aactgcttct gttgtgtgcc ttcttaataa cttctatcct    480

agagaggcta aagttcagtg gaaggtggat aacgcacttc aatctggtaa ctctcaagag    540

tctgttacag agcaagattc taaggactca acttactctc tttcatctac acttactttg    600

tcaaaagcag attacgagaa acacaaagtt tacgcatgcg aagttactca tcaaggactt    660

tcttcaccag ttacaaagtc tttcaataga ggagagtgtt aa                      702
```

```
<210> SEQ ID NO 7
<211> LENGTH: 233
<212> TYPE: PRT
<213> ORGANISM: Artificial Sequence
<220> FEATURE:
<223> OTHER INFORMATION: Translation of optimized light chain sequence

<400> SEQUENCE: 7

Met Gly Trp Ser Cys Ile Ile Leu Phe Leu Val Ala Thr Ala Thr Gly
1               5                   10                  15

Val His Ser Asp Ile Val Met Thr Gln Ser Pro Asp Ser Leu Ala Val
            20                  25                  30

Ser Leu Gly Glu Arg Ala Thr Ile Asn Cys Lys Ala Ser Gln Asp Val
        35                  40                  45

Ser Thr Ala Val Ala Trp Tyr Gln Gln Lys Pro Gly Gln Pro Pro Lys
    50                  55                  60

Leu Leu Ile Ser Trp Ala Ser Thr Arg His Thr Gly Val Pro Asp Arg
65                  70                  75                  80

Phe Ser Gly Ser Gly Ser Gly Thr Asp Phe Thr Leu Thr Ile Ser Ser
                85                  90                  95

Leu Gln Ala Glu Asp Val Ala Val Tyr Tyr Cys Gln Gln His Tyr Thr
            100                 105                 110

Thr Pro Leu Thr Phe Gly Gln Gly Thr Lys Leu Glu Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230


<210> SEQ ID NO 8
<211> LENGTH: 156
<212> TYPE: PRT
<213> ORGANISM: Artificial Sequence
<220> FEATURE:
<223> OTHER INFORMATION: CH1 region of the heavy chain
```

```
<400> SEQUENCE: 8

Asn Glu Lys Leu Lys Ala Arg Val Thr Met Thr Ala Asp Thr Ser Thr
1               5                   10                  15

Ser Thr Ala Tyr Met Glu Leu Arg Ser Leu Arg Ser Asp Asp Thr Ala
            20                  25                  30

Val Tyr Tyr Cys Ala Arg Ser Ala Ser Tyr Gly Asp Tyr Ala Asp Tyr
        35                  40                  45

Trp Gly Gln Gly Thr Thr Val Thr Val Ser Ser Ala Ser Thr Lys Gly
    50                  55                  60

Pro Ser Val Phe Pro Leu Ala Pro Ser Ser Lys Ser Thr Ser Gly Gly
65                  70                  75                  80

Thr Ala Ala Leu Gly Cys Leu Val Lys Asp Tyr Phe Pro Glu Pro Val
                85                  90                  95

Thr Val Ser Trp Asn Ser Gly Ala Leu Thr Ser Gly Val His Thr Phe
            100                 105                 110

Pro Ala Val Leu Gln Ser Ser Gly Leu Tyr Ser Leu Ser Ser Val Val
        115                 120                 125

Thr Val Pro Ser Ser Ser Leu Gly Thr Gln Thr Tyr Ile Cys Asn Val
    130                 135                 140

Asn His Lys Pro Ser Asn Thr Lys Val Asp Lys Arg
145                 150                 155


<210> SEQ ID NO 9
<211> LENGTH: 15
<212> TYPE: PRT
<213> ORGANISM: Artificial Sequence
<220> FEATURE:
<223> OTHER INFORMATION: hinge region of the heavy chain

<400> SEQUENCE: 9

Glu Pro Lys Ser Cys Asp Lys Thr His Thr Cys Pro Pro Cys Pro
1               5                   10                  15


<210> SEQ ID NO 10
<211> LENGTH: 110
<212> TYPE: PRT
<213> ORGANISM: Artificial Sequence
<220> FEATURE:
<223> OTHER INFORMATION: annotates as the CH2 region

<400> SEQUENCE: 10

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
            100                 105                 110


<210> SEQ ID NO 11
<211> LENGTH: 107
<212> TYPE: PRT
```

-continued

```
<213> ORGANISM: Artificial Sequence
<220> FEATURE:
<223> OTHER INFORMATION: CH3 region of the heavy chain

<400> SEQUENCE: 11

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105
```

PRODUCTION OF A MONOCLONAL ANTIBODY THERAPEUTIC AGAINST WEST NILE VIRUS IN PLANTS

CROSS-REFERENCE TO RELATED APPLICATIONS

This application is a National Phase application claiming the benefit of No. PCT/US2011/020635, filed on Jan. 10, 2011, which further claims priority to U.S. Provisional Application No. 61/293,828, filed on Jan. 11, 2010, the entire contents of which are incorporated herein by reference.

FEDERALLY SPONSORED RESEARCH OR DEVELOPMENT

This invention was made with government support under grant number U01 AI075549 awarded by NIH-NIAID. The Government has certain rights in the invention.

FIELD OF THE INVENTION

The present invention relates to plant-based production of recombinant antibodies against West Nile Virus.

BACKGROUND OF THE INVENTION

West Nile virus (WNV) is a member of the Flavivirus genus of the Flaviviridae family, which also includes the Japanese encephalitis virus (JE), Tick-borne encephalitis virus (TBE), St. Louis Encephalitis virus (SLEV), Murray Valley encephalitis virus, dengue virus (including the four serotypes of: DEN-1, DEN-2, DEN-3, and DEN-4), and the family prototype, yellow fever virus (YF). Flavivirus infections are a global public health problem [C. G. Hayes, in The Arboviruses: Epidemiology and Ecology, T. P. Monathy, ed., CRC, Boca Raton, Fla., vol. 5, chap. 49 (1989); M. J. Cardosa, Br Med Bull, 54, pp. 395-405 (1998); Z. Hubalek and J. Halouzka, Emerg Infect Dis, 5, pp. 643-50 (1999)] with about half of the flaviviruses causing human diseases.

WNV is a neurotropic, enveloped virus with a single-stranded, positive polarity, 11 kilobase RNA genome. Until 1999, WNV was found in the Eastern Hemisphere, with wide distribution in Africa, Asia, the Middle East, and Europe (1). In 1999, WNV entered the Western Hemisphere as a point introduction in New York City (2). Greater than 29,000 human cases have been diagnosed with severe WNV infection in the continental United States during the last decade, and many more have been infected and remain undiagnosed. Advanced age is by far the greatest risk factor for severe neurological disease, long-term morbidity, and death (3), although a genetic basis of susceptibility has also been recently identified (4-7).

Historically, there has been a lack of effective and specific antiviral treatment for infection by WNV or other flaviviruses (reviewed in 8). While several small molecules compounds have been recently described with antiviral activity against WNV in vitro, only few have demonstrated efficacy in vivo (9, 10). Interferon (IFN), which is used as part of combination therapy against the distantly related hepatitis C virus, potently inhibits flaviviruses including WNV when used as prophylaxis. However, its effect is markedly attenuated once viral replication has commenced as flavivirus non-structural proteins antagonize IFN signaling pathways (reviewed in 11). Current treatment for WNV infection is supportive and no vaccine or therapeutic agent has been approved for human use. New threats of WNV globally and lack of available treatments warrant studies to develop effective therapeutics and production technologies that can rapidly transfer the candidates into the clinical care settings in a cost-conscious manner.

Even when antibodies are identified as potential prophylactic and or therapeutic medicaments for WNV or other infectious diseases, their ultimate application as beneficial therapeutics is limited by high production costs and scalability associated with the mammalian cell culture production system. Moreover, if biological drugs are too costly to produce for resource poor health care systems and cannot be easily made into generics, their therapeutic potential may never be realized. As such, the development of production platforms that are cost-effective, scalable, and safe for biological therapeutics is urgently needed.

BRIEF SUMMARY OF THE INVENTION

The present invention describes the production of a therapeutic antibody against West Nile Virus that can be rapidly produced in plants at high levels. The method shows that hu-E16 can be purified to >95% purity in a scalable and cGMP manner. The plant-made hu-E16 shows equivalent or superior in vitro and in vivo properties to mammalian hu-E16 in binding affinity, kinetics, and viral neutralization. The antibody produced according to the methods described herein can protects mice from WNV infection in a mouse challenge model both as a prophylactic and a post-infection therapeutic agent, thereby demonstrating the therapeutic and prophylactic potential of the antibodies in a mammalian model.

BRIEF DESCRIPTION OF SEVERAL VIEWS OF THE DRAWINGS

FIG. 3. Antigen recognition and binding kinetics of pHu-E16 for WNV DIII and E protein. A. ELISA of pHu-E16 binding to WNV DIII. Serial dilutions of pHu-E16 were incubated on plates coated with WNV DIII and detected with a HRP-conjugated anti-human kappa antibody. Dilutions of mHu-E16 were used in parallel as reference standards. A plant-produced humanized MAb against Ebola virus GP1 protein (pHu Ebola GP1) was used as a negative control. The OD450 (mean±SD) from three independent experiments are presented. B. Binding of pHu-E16 to DIII of WNV E displayed on yeast cell surface. DIII displaying or negative control yeast cells were stained with pHu-E16, mHu-E16, or a negative control MAb (pHu-Ebola GP1) and processed by flow cytometry. Representative data from several Independent experiments are shown. C. SPR analysis of binding affinity and kinetics of pHu-E16 and mHu-E16 for WNV DIII and E protein. WNV DIII fragment or E ectodomain protein was injected over pHu-E16 or mHu-E16 immobilized to the CM-5 biosensor chip. Binding responses were normalized to the same level of immobilized antibody and analyzed by Langmuir 1:1 interaction fit (black dashed lines). A representative set of SPR binding curves of pHu-E16 for WNV E protein is shown. The results are one of several independent experiments performed in duplicate.

DETAILED DESCRIPTION OF THE INVENTION

Figure 1:
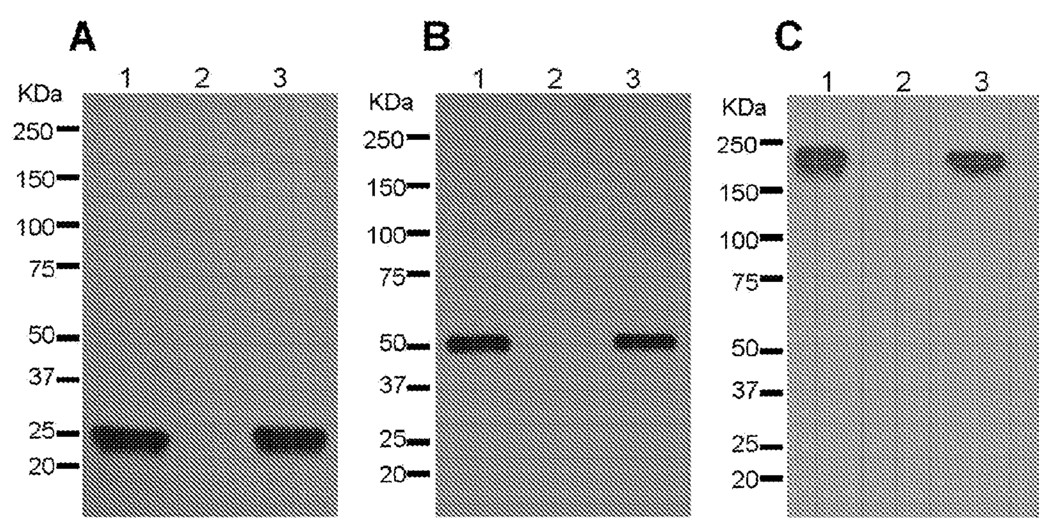
FIG. 1. Western blot analysis of pHu-E16. Leaf protein extracts were separated on 4-20% SDS-PAGE gradient gels under reducing (A and B) or nonreducing (C) condition and blotted onto PVDF membranes. The membranes were incubated with a goat anti-human kappa chain antibody or a goat anti-human gamma chain antibody to detect light chain (A and C) or heavy chain (B). Lane 1, mHu-E16 as a reference standard; lane 2, Protein sample extracted from un-infiltrated leaves; lane 3, Extract from leaves co-infiltrated with Hu-E16 LC and HC constructs.

Despite annual WNV outbreaks in North America there is a lack of effective and specific antiviral treatment (reviewed in 8). The high production costs and limited scalability associated with mammalian cell culture production may restrict the use of therapeutic antibodies against WNV and other flaviviruses in resource-poor settings in the future. Here, we investigated the feasibility of producing in plants a candidate MAb therapeutic against WNV infection. Our results show that (1) plant-derived MAb therapeutics have similar potency as their mammalian-cell counterparts, and (2) production of biological therapeutics in plants provides a platform that can address the cost and scalability issues associated with the mammalian cell culture production system. pHu-E16 retained high-affinity binding and potent neutralizing activity in vitro against WNV and a single dose protected mice against WNV-induced mortality even 4 days after infection at rates that were indistinguishable from mHu-E16. Transgenic plants are suitable for MAb production as they can be rapidly expanded in commercial production without the high-capital investment associated with traditional MAb bioreactor facilities (reviewed in 19). pHu-E16 was expressed rapidly in *N. benthamiana* leaves within 4 to 8 days of infiltration and efficiently assembled into a native IgG form. Without any genetic optimization, pHu-E16 accumulated at an average of 0.8 mg/g of fresh leaf weight, greater than the highest expression level for MAbs in plants ever reported (22). The rapid high-level production and assembly of pHu-E16 convincingly demonstrate the viability of this system for the more large-scale cost249 effective production of MAbs.

It is well-known that downstream processing is an important component of a pharmaceutical protein production technology. In the present invention, there is described a simple three-step extraction and purification scheme that can be used to purify plant-generated Hu-E16 efficiently and in a manner that is scalable for mass production and conforms to cGMP regulations, thereby providing a method for the production of a pharmaceutically acceptable preparation of HU-E16. The rapid high-level accumulation of pHu-E16 in plants and the availability of a scalable and cGMP compliant processing scheme provides advantages over the mammalian cell culture for future low-cost commercial production of Hu-E16 or other therapeutic MAbs.

Hu-E16 derived from mammalian cells is highly potent against almost all WNV strains because it binds a conserved epitope and blocks viral fusion (14). Compared to the parent mHu-E16, pHu-E16 showed equivalent binding kinetics and neutralization activity in vitro. However, pHu-E16 did not show a shift in the neutralization curve to lower antibody concentrations in the presence of human C1q. C1q augments the neutralization potency of mHu-E16 IgG1 by approximately 3-fold (29). SPR studies confirmed that pHu-E16 bound less well to human C1q compared to mHu-E16. This impairment was likely caused by the slightly different carbohydrate modifications on plant-derived antibodies (see Examples). Overall, the functional studies in vitro suggest that pHu-E16 and mHu-E16 had similar but not identical properties.

While plant-derived MAbs or MAb fragments are currently in clinical trials as a cancer vaccine or as topical treatment for tooth decay, and a MAb as post-exposure rabies prophylaxis has been reported (24, 31, 32), our results are the first to demonstrate the efficacy of a plant-produced MAb against a lethal infection several days after exposure. A single dose of pHu-E16 protected mice when administered 2 or 4 days after WNV infection. As WNV has already disseminated to the brain by day 4 (12, 30, 33), pHu-E16 improves survival after the virus has spread into the CNS. Although our in vitro results showed a decrease in the binding to human C1q and an absence of C1q augmented WNV neutralization by pHu-E16, this did not affect potency in vivo in mice. This is likely because Hu-E16 binds mouse C1q less well than human C1q. Indeed, we previously did not observe a difference in protection of the mHu-E16 IgG1 between wild type and $C1q_{-/-}$ mice, and reported a smaller shift in the neutralization potency in vitro of mHu-E16 with murine C1q (29). The N-linked glycosylation of proteins in plants is generally similar to that in mammalian cells. However, plants have unique plant-specific β-1,2-xylose and core α-1,3-fucose residues on complex N-linked glycans and lack terminal β1,4-Gal and N acetylneuraminic acid (Neu5Ac) residues (21). The impact of such differences on the activity of MAb therapeutics in vivo has not been evaluated although glycan variations in the Fc region of IgG modulate the binding and activation of C1q (34, 35). Since pHu-E16 HC has an ER-retention KDEL sequence, it is likely retained in the ER resulting in a predominately high mannose form of glycosylation (31), which contributes to the reduced affinity to C1q (36).

The difference between plant and mammalian glycosylation patterns raises concerns for the immunogenicity of plant-derived MAb therapeutics. The possibility of inducing plant-glycan specific antibodies could reduce therapeutic efficacy by accelerating clearance from plasma, or cause potential adverse effects through immune complex formation. Immunization studies with plant glycoproteins in different animal models have yielded inconsistent results: rats and rabbits develop antibodies to plant specific xylose and α-1,3-fucose, yet mice generate no antibody response against these glycans (37, 38). Moreover, no adverse effects were observed in patients with topical application of plant-produced MAbs with plant unique carbohydrates (39, 40). To date, the immunogenicity of systemic administered plant-produced MAbs has not been evaluated in humans.

To avoid problems associated with plant-specific glycans, "Humanized" *N. benthamiana, Arabidopsis thaliana* and *Lemna minor* plant lines have been generated by genetic knockout or RNA interference (RNAi) strategies (41-43). In these plants, enzymes for the biosynthesis of plant specific glycans are inactivated, resulting in structurally equivalent MAbs as those derived in mammalian cells. Moreover, the glycan uniformity of MAbs produced by these optimized plant lines is better than those from mammalian cell cultures. Indeed, an anti-human CD30 MAb produced from these genetically modified plants had only a single predominant N-glycan species and showed improved antibody-dependent cell-mediated cytotoxicity (ADCC) compared to the same MAb produced in mammalian cells (43). This improvement is most likely due to the removal of fucose, which results in improved FcγR binding of MAbs (44). We speculate that the therapeutic utility of pHu-E16 can be improved by expression in such "humanized" *N. benthamiana* lines.

In brief, the Examples provided below demonstrate that plant-derived MAbs can function effectively as post-exposure therapy against a potentially lethal infectious disease. Plants are an efficient platform to produce Hu-E16 with high-yield, speed, enhanced scalability, and cost-effectiveness, satisfying all major metrics for a successful therapeutic candidate. This technology can be readily applied in the future to antiviral antibodies against other emerging infectious disease threats, and may be most useful in resource poor settings such as the developing world.

E16 is a monoclonal antibody that strongly neutralizes WNV and a humanized version of this antibody has been described in the art that retains its neutralizing activity and avidity (12). In the present invention this antibody was optimized for production of the antibody in a plant-based system. Attached as Appendix A are the Sequence materials showing the optimized sequences for the heavy and light chain for huE16 generated for use in the methods described herein. SEQ ID NO: 1 shows the optimized new E16p sequence-HC variable region (EcoRI-intronless signal sequence-HC-HindIII) used in the present invention. The sequence is translated into an amino acid sequence of SEQ ID NO:2 in which the first 119 amino acids of SEQ ID NO:3, i.e., sequence: QVQLVQSGAEVKKPGASVKVSCKASGYT-FTDYWIEWVRQAPGQGLEWMG DILCGT-GRTRYNEKLKARVTMTADTSTSTAYMEL-RSLRSDDTAVYYCARSASYGDYAD YWGQGTTVTVSS is the VH portion of the sequences, NEKLKARVTM TADTSTSTAYMELRSLRSDDTAVYY-CARSASYGDYADYWGQGTTVTVSSASTKGPSVF PLAPSSKSTSGGTAALGCLVKDYFPEP-VTVSWNSGALTSGVHTFPAVLQSSGLYSLSSVV TVPSSSLGTQTYICNVNHKPSNTKVDKRV (SEQ ID NO:8) depicts the CH1 region of the heavy chain, EPKSCD-KTHTCPPCP (SEQ ID NO:9) is the hinge region of the heavy chain, APELLGGP SVFLFPPKPKDTLMISRTPE-VTCVVVDVSHEDPEVKFNW YVDGVEVHNAKTK-PREEQYNSTYRVVSVLTVLHQDWL-NGKEYKCKVSNKALPAPIEK TISKAK (SEQ ID NO:10) annotates as the CH2 region and GQPREPQVYTLPPSRDEL TKNQVSLTCLVKGFYPS-DIAVEWESNGQPENNYKTTPPVLDSDGS-FFLYSKLTVDKSRW QQGNVFSCSVMHEALH-NHYTQKSLSLSPGK- (SEQ ID NO:11) is the CH3 region of the heavy chain. The entire optimized heavy chain encoding nucleic acid sequence is depicted in SEQ ID NO:4, which encodes a sequence of SEQ ID NO: 5. The sequence of SEQ ID NO:4 is co-expressed in the *N. benthamiana* with a sequence that encodes the humanized light chain of the huE16 antibody. The optimized light chain of huE16 is encoded by the sequence of SEQ ID NO: 6 and encodes the amino acid sequence of the light chain of the huE16 as depicted in SEQ ID NO:7. Coexpression of these two separate chains in *N. benthamiana* as detailed below yields a therapeutic huE16 antibody that has therapeutic and prophylactic properties.

The antibodies of the present invention recognize specific West Nile Virus epitopes. As used herein these terms refer to a molecule (e.g., a peptide) or a fragment of a molecule capable of immunoreactivity with an anti-huE16 antibody and, for example, include a WNV antigenic determinant domain III recognized by the any of the antibodies having a heavy chain/light chain sequence combination of SEQ ID NO:5/SEQ ID NO:7. WNC antigen epitopes can be included in proteins, protein fragments, peptides or the like.

The generalized structure of antibodies or immunoglobulin is well known to those of skill in the art, these molecules are heterotetrameric glycoproteins, typically of about 150,000 daltons, composed of two identical light (L) chains and two identical heavy (H) chains. Each light chain is covalently linked to a heavy chain by one disulfide bond to form a heterodimer, and the heterotrameric molecule is formed through a covalent disulfide linkage between the two identical heavy chains of the heterodimers. Although the light and heavy chains are linked together by one disulfide bond, the number of disulfide linkages between the two heavy chains varies by immunoglobulin isotype. Each heavy and light chain also has regularly spaced intrachain disulfide bridges. Each heavy chain has at the amino-terminus a variable domain (VH), followed by three or four constant domains (CH1, CH2, CH3, and CH4), as well as a hinge region between CH1 and CH2. Each light chain has two domains, an amino-terminal variable domain (VL) and a carboxy-terminal constant domain (CL). The VL domain associates non-covalently with the VH domain, whereas the CL domain is commonly covalently linked to the CH1 domain via a disulfide bond. Particular amino acid residues are believed to form an interface between the light and heavy chain variable domains (Chothia et al., 1985, J. Mol. Biol. 186:651-663.)

Certain domains within the variable domains differ extensively between different antibodies i.e., are "hypervariable." These hypervariable domains contain residues that are directly involved in the binding and specificity of each particular antibody for its specific antigenic determinant. Hypervariability, both in the light chain and the heavy chain variable domains, is concentrated in three segments known as complementarity determining regions (CDRs) or hypervariable loops (HVLs). CDRs are defined by sequence comparison in Kabat et al., 1991, In: Sequences of Proteins of Immunological Interest, 5th Ed. Public Health Service, National Institutes of Health, Bethesda, Md., whereas HVLs are structurally defined according to the three-dimensional structure of the variable domain, as described by Chothia and Lesk, 1987, J. Mol. Biol. 196: 901-917. Where these two methods result in slightly different identifications of a CDR, the structural definition is preferred. As defined by Kabat, CDR-L1 is positioned at about residues 24-34, CDR-L2, at about residues 50-56, and CDR-L3, at about residues 89-97 in the light chain variable domain; CDR-H1 is positioned at about residues 31-35, CDR-H2 at about residues 50-65, and CDR-H3 at about residues 95-102 in the heavy chain variable domain. The CDR1, CDR2, CDR3 of the heavy and light chains therefore define the unique and functional properties specific for a given antibody.

The three CDRs within each of the heavy and light chains are separated by framework regions (FR), which contain sequences that tend to be less variable. From the amino terminus to the carboxy terminus of the heavy and light chain variable domains, the FRs and CDRs are arranged in the order: FR1, CDR1, FR2, CDR2, FR3, CDR3, and FR4. The largely β-sheet configuration of the FRs brings the CDRs within each of the chains into close proximity to each other as well as to the CDRs from the other chain. The resulting conformation contributes to the antigen binding site (see Kabat et al., 1991, NIH Publ. No. 91-3242, Vol. I, pages 647-669), although not all CDR residues are necessarily directly involved in antigen binding.

The terms, "antibody", is used herein in the broadest sense and specifically encompass monoclonal antibodies (including full length monoclonal antibodies), polyclonal antibodies, multispecific antibodies (e.g., bispecific antibodies), and antibody fragments such as variable domains and other portions of antibodies that exhibit a desired biological activity, e.g., WNV binding and or neutralizing.

The term "monoclonal antibody" (mAb) refers to an antibody of a population of substantially homogeneous antibodies; that is, the individual antibodies in that population are identical except for naturally occurring mutations that may be present in minor amounts. Monoclonal antibodies are highly specific, being directed against a single antigenic determinant, an "epitope". Therefore, the modifier "monoclonal" is indicative of a substantially homogeneous population of antibodies directed to the identical epitope and is not to be construed as requiring production of the antibody by any particular method. It should be understood that monoclonal antibodies can be made by any technique or methodology known in the art; including e.g., the hybridoma method (Kohler et al., 1975, Nature 256:495), or recombinant DNA methods known in the art (see, e.g., U.S. Pat. No. 4,816,567), or methods of isolation of monoclonal recombinantly produced using phage antibody libraries, using techniques described in Clackson et al., 1991, Nature 352: 624-628, and Marks et al., 1991, J. Mol. Biol. 222: 581-597.

Chimeric antibodies consist of the heavy and light chain variable regions of an antibody from one species (e.g., a non-human mammal such as a mouse) and the heavy and light chain constant regions of another species (e.g., human) antibody and can be obtained by linking the DNA sequences encoding the variable regions of the antibody from the first species (e.g., mouse) to the DNA sequences for the constant regions of the antibody from the second (e.g. human) species and transforming a host with an expression vector containing the linked sequences to allow it to produce a chimeric antibody. Alternatively, the chimeric antibody also could be one in which one or more regions or domains of the heavy and/or light chain is identical with, homologous to, or a variant of the corresponding sequence in a monoclonal antibody from another immunoglobulin class or isotype, or from a consensus sequence. Chimeric antibodies can include fragments of such antibodies, provided that the antibody fragment exhibits the desired biological activity of its parent antibody, for example binding to the same epitope (see, e.g., U.S. Pat. No. 4,816,567; and Morrison et al., 1984, Proc. Natl. Acad. Sci. USA 81: 6851-6855).

The methods of the invention can also be used to prepare antibody fragments. The terms, "antibody fragment", refer to a portion of a full length huE16 antibody, in which a variable region or a functional capability is retained, for example, specific West Nile Virus epitope binding. Examples of antibody fragments include, but are not limited to, a Fab, Fab', F(ab')2, Fd, Fv, scFv and scFv-Fc fragment, a diabody, a linear antibody, a single-chain antibody, a minibody, a diabody formed from antibody fragments, and multispecific antibodies formed from antibody fragments.

Full length antibodies can be treated with enzymes such as papain or pepsin to generate useful antibody fragments. Papain digestion is used to produces two identical antigen-binding antibody fragments called "Fab" fragments, each with a single antigen-binding site, and a residual "Fc" fragment. The Fab fragment also contains the constant domain of the light chain and the CH1 domain of the heavy chain. Pepsin treatment yields a F(ab')2 fragment that has two antigen-binding sites and is still capable of cross-linking antigen.

Fab' fragments differ from Fab fragments by the presence of additional residues including one or more cysteines from the antibody hinge region at the C-terminus of the CH1 domain. F(ab')2 antibody fragments are pairs of Fab' fragments linked by cysteine residues in the hinge region. Other chemical couplings of antibody fragments are also known.

"Fv" fragment is contains a complete antigen-recognition and binding site consisting of a dimer of one heavy and one light chain variable domain in tight, non-covalent association. In this configuration, the three CDRs of each variable domain interact to define an antigen-biding site on the surface of the VH-VL dimer. Collectively, the six CDRs confer antigen-binding specificity to the antibody.

A "single-chain Fv" or "scFv" antibody fragment is a single chain Fv variant comprising the VH and VL domains of an antibody where the domains are present in a single polypeptide chain. The single chain Fv is capable of recognizing and binding antigen. The scFv polypeptide may optionally also contain a polypeptide linker positioned between the VH and VL domains in order to facilitate formation of a desired three-dimensional structure for antigen binding by the scFv (see, e.g., Pluckthun, 1994, In The Pharmacology of monoclonal Antibodies, Vol. 113, Rosenburg and Moore eds., Springer-Verlag, New York, pp. 269-315).

Other recognized antibody fragments include those that comprise a pair of tandem Fd segments (VH-CH1-VH-CH1) to form a pair of antigen binding regions. These "linear antibodies" can be bispecific or monospecific as described in, for example, Zapata et al. 1995, Protein Eng. 8(10):1057-1062.

Any of the above antibody fragments or variants can be produced by the methods described herein and isolated for use as therapeutic and or prophylactic medicaments. An will be prepared by at least one purification step in which the recombinant cellular material is removed. The methods described below are scaleable for the production of large quantities of the huE16 antibody for therapeutic and or prophylactic uses against WNV infection.

EXAMPLES

Example 1

Materials and Methods

Construction of pHu-E16 MAb Expression Vectors.

The coding sequences of Hu-E16 MAb LC and HC (12) were optimized in silico with *N. benthamiana*-optimized codons using an algorithm described in (26). An 18-bp sequence coding for a 'SEKDEL' hexapeptide ER-retention signal was added to the C-terminus of the HC gene. Optimized LC and HC, sequences were synthesized (DNA 2.0) and cloned into the 5' modules of plant expression vectors pICH21595 and pICH11599 of the MagnICON system as described previously (22).

Agroinfiltration of *N. benthamiana.*

Plant expression vectors were individually transformed into *Agrobacterium tumefaciens* GV3101 by electroporation as previously described (45). Wild-type *N. benthamiana* plants were grown in a greenhouse with 16/8 hr light/dark cycle at 25° C. for 5 weeks. Plant leaves were co-Agroinfiltrated with GV3101 strains containing the LC and HC 5' modules along with their respective 3' modules and an integrase construct as described previously (22).

Extraction of Total Protein from Plant Leaves.

Agroinfiltrated *N. benthamiana* leaves were harvested on days 4, 5, 6, 7, 8, 9, and 10 days post infiltration (dpi) for evaluating the temporal pattern of pHu-E16 MAb expression. For other protein analysis, plant leaves were harvested 7 dpi. Total leaf protein was extracted by homogenization with extraction buffer (PBS, 1 mM EDTA, 10 mg/ml sodium ascorbate, 10 μg/ml leupeptin, 0.3 mg/ml phenylmethylsufonylflouride) using a FastPrep machine (Bio101) following the manufacture's instruction. The crude plant extract was clarified by centrifugation at 14,000×g for 10 min at 4° C.

SDS-PAGE and Western Blot.

SDS-PAGE and Western blotting were performed as described previously (46). Protein samples were subjected to 4-20% gradient SDS-PAGE under reducing (5% v/v β-mercaptoethanol) or non-reducing conditions. Gels were then either stained with Coomassie blue or used to transfer proteins onto PVDF membranes. HRP-conjugated antibodies against human-kappa LC or gamma HC (Southern Biotech) were used for western blot analysis.

ELISA.

An ELISA designed to detect the assembled form of MAb (with both LC and HC) was performed to quantify pHu-E16 expression as described previously (22). Plates were coated with a goat anti-human gamma HC antibody (Southern Biotech). After incubation with plant protein extract, a HRP-conjugated anti-human-kappa LC antibody was used as the detection antibody. mHu-E16 was used as reference standard (12).

The ELISA for examining the binding of pHu-E16 to WNV E DIII was performed based on an earlier publication (27). DIII (amino acids 296-415) protein of the New York 1999 strain of WNV purified from *E. coli* (27) was immobilized on microtiter plates. An HRP-conjugated anti-human-kappa LC antibody was used as the detection antibody. The plates were developed with TMB substrate (KPL Inc).

Purification of pHu-E16.

pHu-E16 was purified from *N. benthamiana* leaves by a three-step purification protocol comprised of ammonium sulfate precipitation, protein A affinity and DEAE-anion exchange chromatographies.

*N. benthamiana* leaves infiltrated with hu-E16 MAb constructs were harvested on 7 dpi and homogenized with the extraction buffer (PBS, 1 mM EDTA, 10 mg/ml sodium ascorbate, 10 μg/ml leupeptin, 0.3 mg/ml PMSF). Crude extract was filtered through Miracloth and centrifuged at 17,700×g for 30 min at 4° C. to remove cell debris. Ammonium sulfate was added slowly to the clarified plant extracts to 25% saturation with thorough mixing at 4° C. The sample was centrifuged at 17,700×g for 30 min at 4° C. and the pellet as saved for analysis. The 25% ammonium sulfate supernatant was further processed by adding ammonium sulfate to 50% saturation. The sample was again centrifuged at 17,700×g for 30 min and the supernatant was discarded. The 50% ammonium sulfate pellet was resuspended in PBS and then applied to a MABSELECT Protein A column (GE Healthcare, Piscataway, N.J.). After washing with PBS, the column was eluted with 50 mM sodium citrate, pH 2.5. The eluate was neutralized immediately with 1M Tris-base to a final pH of 7.0 and further purified by DEAE anion exchange chromatography with DEAE SEPHAROSE FF 26/20 resin (GE Healthcare, Piscataway, N.J.). Purified pHu-E16 was collected in the DEAE flow-through fraction. The purity of pHu-E 16 was determined by quantitating Coomassie blue-stained protein bands on SDS-PAGE using a densitometer. Levels of residual DNA, Protein A and endotoxin in the final purified samples were quantified by using commercial PICOGREEN dsDNA quantitation (Invitrogen, Carlsbad, Calif.), protein A ELISA (Cygnus Technologies, Southport, N.C.), and QCL-1000 Chromogenic LAL Endpoint assay kits (Lonza, Allendale, N.J.), respectively, based on the manufacturers' instructions.

Cells, Reporter Virus Particles, and Antibody Neutralization.

BHK21-15, C6/36, and Raji-DC-SIGNR cells were maintained as described (13, 28, 47). WNV reporter virus particles (RVP), which encode GFP, were produced in HEK293T cells as described (13, 28). The neutralization potency of pHu-E16 or mHu-E16 was measured in the presence or absence of purified human C1q protein (Complement Technologies). Neutralization potency was calculated as a function of the concentration of antibody required to block 50% of the infection events using non-linear regression analysis (GraphPad-Prism4). mHu-E16 was produced in CHO cells and purified by protein A affinity and size exclusion chromatography as described (12).

Recombinant Protein Expression and Yeast Surface Display.

The WNV E ectodomain (residues 1-404) and DIII (residues 296-404) of the New York 1999 strain were cloned into the pET21a bacterial expression plasmid (EMD Biosciences) as described previously (27). All constructs were expressed in *E. coli* and purified using an oxidative refolding protocol (27). Refolded protein was separated from aggregates on a Superdex 75 or 200, 16/60 size-exclusion column using fast protein liquid chromatography (GE Healthcare). Yeast expressing WNV DIII were generated and stained with MAbs as described (12). Yeast cells were analyzed with a Becton Dickinson FACSCalibur flow cytometer.

Surface Plasmon Resonance.

Affinity measurement of MAb for DIII or E ectodomain of WNV was performed by surface plasmon resonance (SPR). The binding of human C1q to mHu-E16 and pHu-E16 was also analyzed by SPR.

Affinity measurement of MAb for DIII of WNV was performed by surface plasmon resonance (SPR, BIAcore 3000 biosensor, Biacore, Inc). pHu-E16 or mHu-E16 were immobilized on the CM-5 sensor chip (~500 RU) by amine coupling kit as recommended by the manufacturer. Subsequently, purified DIII or E ectodomain was injected at concentrations of 3.1, 6.3, 12.5, 25, 50 and 100 nM, a flow rate of 70 μl/minute for 180 sec, and then allowed to dissociate over 180 sec. Regeneration of antibody surfaces was performed by pulse injection of 10 mM glycine pH 1.5. Binding responses were normalized to the same level of immobilized antibody and analyzed using the BIA evaluation 4.1 software. Kinetic constants, k (a) and k (d), were estimated by global fitting analysis of the association/dissociation curves to the 1:1 Langmuir interaction model. The equilibrium dissociation constant (KD) was calculated as $KD=k_{(d)}/k_{(a)}$.

The binding of human C1q to mHu-E16 and pHu-E16 was analyzed by SPR. WNV DIII was immobilized on the CM-5 sensor chip by amine coupling. MAb was bound to the DIII surface at approximately 1000 RU, followed by injection of C1q at 24 nM and a flow rate of 30 μl/min for 60 sec with dissociation time of 60 sec. Between experiments, the naked antigen surface was regenerated by pulse injection of 10 mM glycine pH 1.5. All binding experiments were performed in 10 mM Hepes, pH 7.4, 150 mM NaCl, 3 mM EDTA, and 0.005% P20 surfactant.

Efficacy of MAbs In Vivo.

All mice were housed in a pathogen-free mouse facility. Studies were performed with approval from the Washington University School of Medicine Animal Safety Committee. Mice received a single dose of purified pHu-E16 or mHu-E16 by intraperitoneal injection the same day, two days after, or four days after footpad infection with $10_2$ plaque forming units (PFU) of WNV strain 3000.0259. Five week-old wild type C57BL/6 mice were purchased commercially (Jackson Laboratories). Kaplan-Meier analysis of survival data was performed using the log-rank test. IC50 analyses were performed by non-linear regression and statistical significances were determined using analysis of variance (ANOVA) and F-tests.

Example 2

Expression and Assembly of Hu-E16 MAb in Plants

Figure 2:
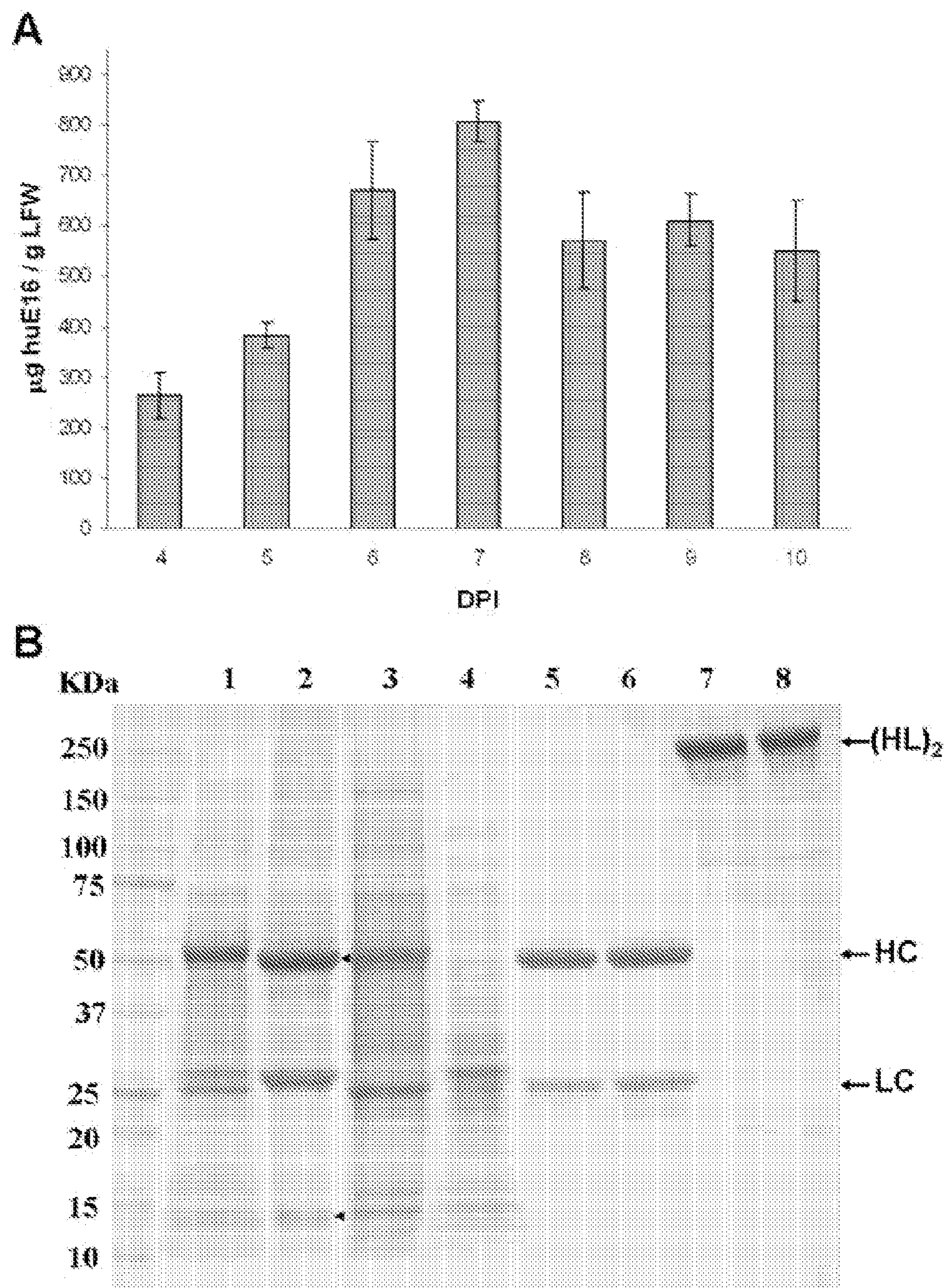
FIG. 2. Expression and purification of Hu-E16 mAb in *N. benthamiana* plants. *N. benthamiana* leaves were co-infiltrated with Hu-E16 LC and HC constructs. Leaf proteins were extracted on days 4 to 10 after agroinfiltration (A) or on day 7 after agroinfiltration (B). A. Protein extracts were analyzed with an ELISA that detects the assembled form of pHu-E16 MAb. Mean±standard deviation (SD) of samples from three independent infiltration experiments are presented. B. Leaf protein extract was purified and analyzed on a 4-20% SDS-PAGE gel under reducing (Lanes 1-6) or nonreducing (Lanes 7 and 8) condition. Lane 1, Clarified plant extract; lane 2, Plant proteins removed by 25% ammonium sulfate precipitation; lane 3, 50% ammonium sulfate pellet fraction resuspended for Protein A Chromatography; lane 4, Protein A flow-through fraction; lanes 5 and 7, Purified pHu-E16 mAb in the Protein A eluate; lanes 6 and 8, mHu-E16 as a reference standard. ◀: RuBisCo large and small subunits; : light (LC), heavy (HC) chain, and assembled form $(HL)_2$ of Hu-E16 MAb.

As a first test of the feasibility of developing a plant-derived Hu-E16 therapeutic, we needed to demonstrate that plants could express and assemble Hu-E16. To ensure high-level expression of Hu-E16 in plants, the coding sequences of Hu-E16 light chain (LC) and heavy chain (HC) were optimized in silico with *N. benthamiana*-optimized codons (26). Optimized LC and HC sequences were cloned into the 5' modules of plant expression vectors of the MagnICON system (22) and transformed into *Agrobacterium tumefacient*. To co-express Hu-E16 LC and HC, *A. tumefacient* strains harboring the LC and HC 5' modules were co-delivered into *N. benthamiana* leaves along with their respective 3' modules and an integrase construct through vacuum infiltration (22). Western blot analysis confirmed that the LC and HC of pHu-E16 were produced in leaves with the expected molecular weights of 25 kDa and 50 kDa, respectively (FIGS. 1A and B). Western blot analysis under non-reducing conditions showed a pHu-E16 MAb band with a molecular weight of ~170 kDa, indicating assembly into its tetrameric (2HC+2 LC) form (FIG. 1C). Comparison of bands from reducing and non-reducing gels also confirmed no cleavage of the fully assembled MAb since only intact LC and HC bands. The assembly of pHu-E16 was corroborated by an ELISA that detects the assembled form of E16 (HC capture, LC probe) (FIG. 2A). ELISA results also indicated that pHu-E16 reached the highest level of production 7 days post infiltration with *A. tumefacient* containing the HC and LC constructs, with an average accumulation of 8.1 mg/g leaf fresh weight (LFW). This level is greater than the highest expression level for MAbs in plants ever reported (22) and convincingly demonstrates that plants can rapidly express fully-assembled pHu-E16 at high levels.

Example 3

Purification and Scale-Up Production of pHu-E16

For plant-produced pHu-E16 to become a viable WNV therapeutic candidate, an efficient purification scheme from plant tissue must be developed. pHu-E16 was extracted and purified by a three-step purification protocol comprised of ammonium sulfate precipitation, protein A affinity and DEAE-anion exchange chromatographies. Precipitation with 35% ammonium sulfate effectively removed the most abundant plant host protein, the photosynthetic enzyme RuBisCo, and other plant proteins (FIG. 2B, Lane 2). Protein A affinity chromatography removed the remaining contaminating proteins and enriched pHu-E16 to greater than 95% purity (FIG. 2B, Lane 5). In the presence of a reducing agent, purified pHu-E16 was detected as the HC and LC (migration at ~50 and 25 kDa) in the same stoichiometric ratio as the Hu-E16 produced in mammalian cells (FIG. 2B, Lanes 5 and 6). Under oxidizing conditions, purified pHu-E16 antibody assembled in its tetrameric form (FIG. 2B, Lane 7). For future clinical testing and cGMP production, an ion exchange chromatographic step was added to eliminate residual DNA, endotoxin, and Protein A from the final purified product. Contaminants and/or impurities were efficiently removed using this purification scheme so that levels in the final pHu-E16 product were below the Food and Drug Administration specifications for injectable human MAb pharmaceuticals (Table 1). To validate the scalability of our purification protocol, we purified pHu-E16 purification at different scales of plant materials ranging from 10 to 5,000 grams. Our protocol produced highly purified pHu-E16 from *N. benthamiana* plants with consistent recovery among batches of different scale (Table 1). In total, >5 g of hu-E16 was purified from 16 kg of plant material for in vitro and in vivo studies.

TABLE 1

Characterization of pHu-E16 mAb purification scheme

| LFW (g) | Recovery (%) | Purity | Residual DNA (ng/ml) | Residual Protein A (ng/ml) | Endotoxin (EU/ml) |
|---|---|---|---|---|---|
| 10 | 57.52 ± 2.59 | >95% | <1 | 9.77 ± 3.02 | 3.78 ± 1.52 |
| 100 | 51.71 ± 2.86 | >95% | <1 | 11.65 ± 2.15 | 3.57 ± 2.60 |
| 500 | 45.77 ± 4.84 | >95% | <1 | 12.04 ± 3.42 | 2.94 ± 1.57 |
| 5000 | 48.76 ± 6.06 | >95% | <1 | 10.33 ± 6.65 | 4.12 ± 2.93 |

Example 4 pHu-E16 Retains Antigen Binding Activity

To begin to establish a similarity of structural, biochemical and functional properties between plant- and mammalian cell-derived Hu-E16, we compared their recognition and binding kinetics for WNV E proteins or domains in three assays: (1) The binding of pHu-E16 to WNV E DIII was determined by ELISA in which DIII was immobilized (27). pHu-E16 and mHu-E16 bound in a similar manner to DIII (FIG. 3A). (2) Recognition of pHu-E16 for DIII was examined in a binding assay with yeast that display DIII on their surface. Flow cytometric analysis showed that the percentage of positive yeast and the mean fluorescence intensity of binding by pHu-E16 and mHu-E16 were virtually identical (FIG. 3B). (3) To assess the binding of pHu-E16 more quantitatively, a surface plasmon resonance (SPR) assay was utilized with purified pHu-E16 or mHu-E16 immobilized on a BIAcore chip. Monomeric WNV E protein and E domain III were generated, and flowed across the solid-phase Hu-E16 mAbs at six different concentrations. pHu-E16 had almost identical binding affinity and kinetics for WNV E protein and DIII compared to its mHu-E16 counterpart (FIG. 3C).

Example 5

Neutralizing Activity of pHu-E16

Figure 4:
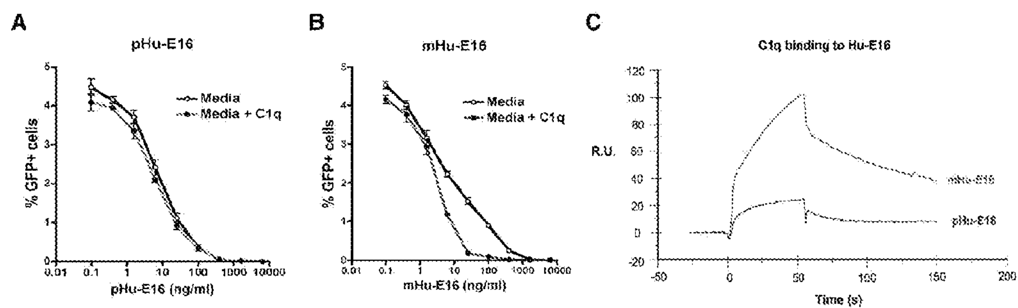
FIG. 4. The neutralizing activity of mHu-E16 and pHu-E16 and effect of C1q. Serial dilutions of (A) mHu-E16 or (B) pHu-E16 were incubated with WNV RVP in the presence of media or 50 μg/ml of purified human C1q prior to infection of Raji-CD SIGN-R cells. Forty hours later, cells were fixed and analyzed by flow cytometry for GFP expression. Data are representative of at least three independent experiments performed in triplicate and bars represent the standard error of the mean. C. SPR analysis of C1q binding to mHu-E16 and pHu-E16. C1q (24 nM) was injected over captured antibody on immobilized DIII fragment. Data are representative of several independent experiments.

To evaluate the neutralization potential of pHu-E16, we used a validated and quantitative flow cytometry-based neutralization assay (28) that measures antibody inhibition of infection with WNV reporter virus particles (RVP). WNV RVP were mixed with varying concentrations of pHu-E16 or mHu-E16 MAbs, and then incubated with permissive Raji-DC-SIGN-R cells. Neutralization was monitored as a function of GFP fluorescence by flow cytometry at 40 hours after infection. pHu-E16 neutralized WNV infection equivalently compared to mHu-E16 (FIGS. 4A and B). Recent studies have suggested that the complement component C1q augments the neutralizing potency of mHu-E16 (29). In the presence of purified C1q, the neutralization curve of mHu-E16 but not pHu-E16 showed a shift to the left, indicating greater inhibition at lower antibody concentrations. This suggests that slightly different carbohydrate modifications on the plant-derived MAb impaired an interaction with C1q as compared to mHu-E16. This was confirmed by an SPR assay as pHu-E16 showed lower binding to C1q (FIG. 4C). Overall, the binding and neutralization studies in vitro suggest that pHu-E16 and mHu-E16 had similar but not identical functional properties.

Example 6 pHu-E16 Protects Against Lethal WNV Infection

Prophylaxis Studies.

Figure 5:
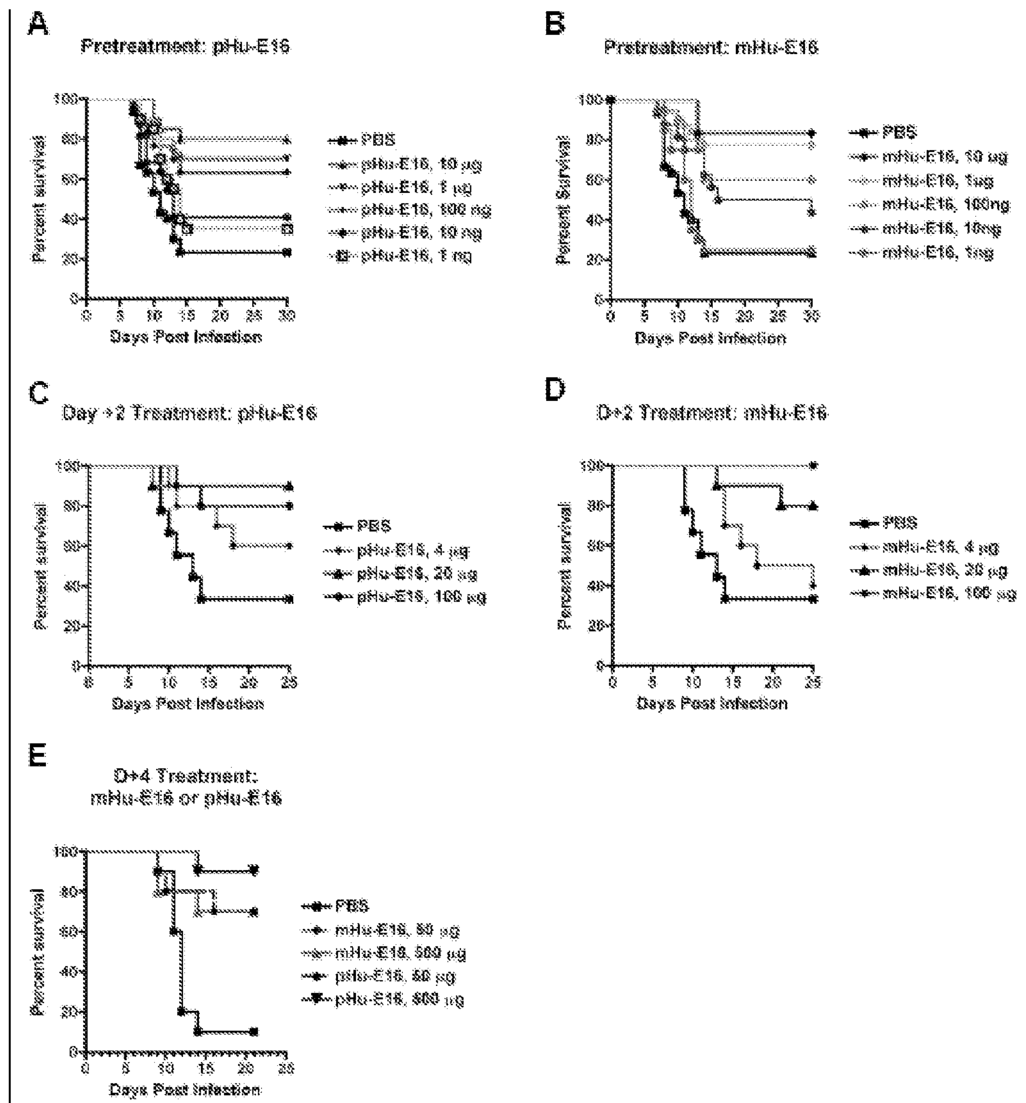
FIG. 5. pHu-E16 and mHu-E16 mediated protection in mice. A-B. Five week-old C57BL/6 mice were passively transferred saline or serial 10-fold increases in dose (ranging from 0.001 to 10 μg, N>20 per dose) of pHu-E16 (A) or mHu-E16 (B) via an intraperitoneal route on the same day as subcutaneous infection with $10_2$ PFU of WNV. Survival data from at least two independent experiments were analyzed by log rank test, and IC50s were calculated by non-linear regression of survival percentage at each MAb dose. As indicated in the text, both pHu-E16 and mHu-E16 were highly protective, there was no significant difference in IC50 values (P>0.6). C-E. Wild type C57BL/6 mice were infected with $10_2$ PFU of WNV and then given a single dose of the indicated doses of pHu-E16 or mHu-E16 via an intraperitoneal route at (C and D) day +2 or (E) day +4 after infection. Survival data from at least two independent experiments (N=20 per dose) were analyzed by the log-rank test.

Although the functional studies suggested similar activity of the pHu-E16, it was essential to confirm this in vivo. Pre-treatment studies were performed in 5 week-old wild type C57BL/6 mice (N>20, per group) to compare the concentrations of pHu-E16 and mHu-E16 that prevent severe WNV infection. Mice were infected with $10_2$ PFU of WNV, which causes a baseline mortality of 80 to 90% (30). Increasing amounts (0.001 to 10 μg) of pHu-E16 or mHu-E16 were administered as a single dose on the day of infection. Mice were significantly protected when administered as little as 0.1 μg of pHu-E16 (FIG. 5A, P<0.001). Greater than 80% of mice were protected from lethal infection when 10 μg of pHu-E16 was administered (P<0.0001). Protection against WNV lethality achieved by pHu-E16 was similar in magnitude as that observed with mHu-E16 (pHu-E16, IC50=0.19 μg, mHu-E16, IC50=0.15 μg, P>0.6) (FIGS. 5A and B).

Therapeutic Studies.

Post-exposure treatment studies were performed to confirm the therapeutic activity of pHu-E16 when administered at a specific time point after infection in mice. Mice were passively administered a single dose (4 to 100 μg) of pHu-E16 or mHu-E16 by intraperitoneal injection at day 2 after subcutaneous inoculation of $10_2$ PFU of WNV (FIGS. 5C and D). Notably, 20 μg of pHu-E16 protected most mice from lethal infection when given 2 days after WNV inoculation and a single injection of as low as 4 μg also prevented mortality; these results were similar to that observed in experiments with mHu-E16 performed in parallel. Since WNV spreads to the brain in mice by day 4 after infection (12), we also investigated the therapeutic efficacy of pHu-E16 at this later time point (FIG. 5E). A single administration of 50 μg of pHu-E16 protected up to 70% of mice from lethal infection and a 90% survival rate was achieved with a single 500 μg dose, results that were equivalent in protection to mHu-E16. Overall, pHu-E16 appeared as potent as mHu-E16 in mice.

REFERENCES

1. Hubalek Z, Halouzka J (1999) West Nile fever—a reemerging mosquito-borne viral disease in Europe. *Emerg Inf Dis.* 5: 643-650.
2. Petersen S V, Thiel S, Jensenius J C (2001) The mannan-binding lectin pathway of complement activation: biology and disease association. *Mol Immunol.* 38:133-149.
3. Bode A V, et al. (2006) West Nile virus disease: a descriptive study of 228 patients hospitalized in a 4-county region of Colorado in 2003. *Clin Infect Dis.* 42: 1234-1240.
4. Glass W G, et al. (2006) CCR5 deficiency increases risk of symptomatic West Nile virus infection. *J Exp Med.* 203: 35-40.
5. Diamond M S, Klein R S (2006) A genetic basis for human susceptibility to West Nile virus. *Trends Microbiol.* 14: 287-289.
6. Lim J K, et al. (2009) Genetic variation in OAS1 is a risk factor for initial infection with West Nile virus in man. *PLoS Pathog.* 5: e1000321.
7. Lim J K, et al. (2008) Genetic deficiency of chemokine receptor CCR5 is a strong risk factor for symptomatic West Nile virus infection: a meta-analysis of 4 cohorts in the US epidemic. *J Infect Dis.* 197: 262-265.
8. Diamond M S (2009) Progress on the development of therapeutics against West Nile virus. *Antiviral Res.* 83: 214-227.
9. Furuta Y, et al. (2009) T-705 (favipiravir) and related compounds: Novel broad spectrum inhibitors of RNA viral infections. *Antiviral Res.* 82: 95-102.
10. Morrey J D, et al. (2008) Efficacy of orally administered T-705 pyrazine analog on lethal West Nile virus infection in rodents. *Antiviral Res.* 80: 377-379.
11. Diamond M S (2009) Mechanisms of Evasion of the Type I Interferon Antiviral Response by Flaviviruses. *Interferon Cytokine Res.* 29: 521-530.
12. Oliphant T, et al. (2005) Development of a humanized monoclonal antibody with therapeutic potential against West Nile virus. *Nat Med.* 11: 522-530.
13. Pierson T C, et al. (2007) The stoichiometry of antibody-mediated neutralization and enhancement of West Nile virus infection. *Cell Host Microbe.* 1: 135-145.
14. Thompson B S, et al. (2009) A therapeutic antibody against west nile virus neutralizes infection by blocking fusion within endosomes. *PLoS Pathog.* 5:e1000453.
15. Morrey J D, et al. (2006) Humanized monoclonal antibody against West Nile virus envelope protein administered after neuronal infection protects against lethal encephalitis in hamsters. *J Infect Dis.* 194: 1300-1308.
16. Morrey J D, et al. (2007) Defining limits of treatment with humanized neutralizing monoclonal antibody for West Nile virus neurological infection in a hamster model. *Antimicrob Agents Chemother.* 51: 2396-2402.

17. Morrey J D, et al. (2008) West Nile virus-induced acute flaccid paralysis is prevented by monoclonal antibody treatment when administered after infection of spinal cord neurons. *J Neurovirol.* 14: 152-163.

18. Samuel M A, et al. (2007) Axonal transport mediates West Nile virus entry into the central nervous system and induces acute flaccid paralysis. *Proc Natl Acad Sci USA.* 104: 17140-17145.

19. Chen Q (2008) Expression and purification of pharmaceutical proteins in plants *Biol Eng.* 1: 291-321.

20. Vitale A, Pedrazzini E (2005) Recombinant pharmaceuticals from plants: the plant endomembrane system as bioreactor. *Mol Interv.* 5: 216-225.

21. Gomord V, et al. (2004) Production and glycosylation of plant-made pharmaceuticals: the antibodies as a challenge. *Plant Biotechnol J.* 2: 83-100.

22. Giritch A, et al. (2006) Rapid high-yield expression of full-size IgG antibodies in plants coinfected with noncompeting viral vectors. *Proc Natl Acad Sci USA.* 103: 14701-14706.

23. McLean M D, et al. (2007) A Human Anti-Pseudomonas aeruginosa Serotype O6ad Immunoglobulin G1 Expressed in Transgenic Tobacco Is Capable of Recruiting Immune System Effector Function In Vitro. *Antimicrob. Agents Chemother.* 51: 3322-3328.

24. McCormick A A, et al. (2008) Plant-produced idiotype vaccines for the treatment of non-Hodgkin's lymphoma: Safety and immunogenicity in a phase I clinical study. *Proc Natl Acad Sci USA.* 105: 10131-10136.

25. Weintraub J A, et al. (2005) Clinical trial of a plant-derived antibody on recolonization of mutans streptococci. *Caries Res.* 39: 241-250.

26. Villalobos A, et al. (2006) Gene Designer: a synthetic biology tool for constructing artificial DNA segments. *BMC Bioinformatics.* 7: 285.

27. Oliphant T, et al. (2007) Induction of epitope-specific neutralizing antibodies against West Nile virus. *J Virol.* 81: 11828-11839.

28. Pierson T C, et al. (2006) A rapid and quantitative assay for measuring antibody mediated neutralization of West Nile virus infection. *Virology.* 346: 53-65.

29. Mehlhop E, et al. (2009) Complement protein C1q reduces the stoichiometric threshold for antibody-mediated neutralization of West Nile virus. *Cell Host Microbe.* 6: 381-391.

30. Engle M, Diamond M S (2003) Antibody prophylaxis and therapy against West Nile Virus infection in wild type and immunodeficient mice. *J Virol.* 77: 12941-12949.

31. Ko K, et al. (2003) Function and glycosylation of plant-derived antiviral monoclonal antibody. *Proc Natl Acad Sci USA.* 100: 8013-8018.

32. Ko K, Koprowski H (2005) Plant biopharming of monoclonal antibodies. *Virus Research.* 111: 93-100.

33. Diamond M S, et al. (2003) B cells and antibody play critical roles in the immediate defense of disseminated infection by West Nile encephalitis virus. *J Virol.* 77: 2578-2586.

34. Raju T S (2008) Terminal sugars of Fc glycans influence antibody effector functions of IgGs. *Curr Opin Immunol.* 20: 471-478.

35. Wang F, et al. (2006) Structural and functional characterization of glycosylation in an immunoglobulin G1 to *Cryptococcus neoformans* glucuronoxylomannan. *Mol Immunol.* 43: 987-998.

36. Qun Z, et al. (2008) Development of a simple and rapid method for producing non-fucosylated oligomannose containing antibodies with increased effector function. *Biotechnol Bioeng.* 99: 652-665.

37. Chargelegue D, et al. (2000) A murine monoclonal antibody produced in transgenic plants with plant-specific glycans is not immunogenic in mice. *Transgenic Res.* 9: 187-194.

38. Jin C, et al. (2008) A plant derived human monoclonal antibody induces an anticarbohydrate immune response in rabbits. *Glycobiology.*

39. Zeitlin L, et al. (1998) A humanized monoclonal antibody produced in transgenic plants for immunoprotection of the vagina against genital herpes. *Nat Biotech.* 16: 1361-1364.

40. Ma J K, et al. (1998) Characterization of a recombinant plant monoclonal secretory antibody and preventive immunotherapy in humans. *Nat Med.* 4: 601-606.

41. Schahs M, et al. (2007) Production of a monoclonal antibody in plants with a humanized N-glycosylation pattern. *Plant Biotechnol J.* 5: 657-663.

42. Strasser R, et al. (2008) Generation of glyco-engineered *Nicotiana benthamiana* for the production of monoclonal antibodies with a homogeneous human-like N glycan structure. *Plant Biotechnol J.* 6: 392-402.

43. Cox K M, et al. (2006) Glycan optimization of a human monoclonal antibody in the aquatic plant *Lemna minor. Nat Biotechnol.* 24: 1591-1597.

44. Shields R L, et al. (2002) Lack of fucose on human IgG1 N-linked oligosaccharide improves binding to human Fcgamma RIII and antibody-dependent cellular toxicity. *J Biol Chem.* 277: 26733-26740.

45. Huang Z, et al. (2009) A DNA replicon system for rapid high-level production of virus-like particles in plants. *Biotechnol Bioeng.* 103: 706-714.

46. Santi L, et al. (2008) An efficient plant viral expression system generating orally immunogenic Norwalk virus-like particles. *Vaccine.* 26: 1846-1854.

47. Pierson T C, et al. (2005) An infectious West Nile Virus that expresses a GFP reporter gene. *Virology.* 334: 28-40.

The invention claimed is:

1. A method for producing an isolated humanized E16 antibody (hu-E16) and fragments thereof against West Nile Virus (WNV), comprising:

a) transfecting a *N. benthamiana* plant cell with a nucleic acid molecule having SEQ ID NO:4, which encodes a heavy chain sequence of hu-E16, and a nucleic acid molecule having SEQ ID NO:6, which encodes a light chain sequence of hu-E16, wherein said heavy and light chain sequences of hu-E16 comprise *N. benthamiana*-optimized codons;

b) expressing said heavy and light sequences of hu-E16 in said transfected *N. benthamiana* plant cell;

c) growing said *N. benthamiana* plant; and d) purifying the hu-E16 from the leaves of said *N. benthamiana* plant, wherein said hu-E16 neutralizes WNV in vitro and in vivo.

2. The method of claim 1, wherein said purifying comprises:

a) ammonium sulfate precipitation comprising an initial precipitation at 25% ammonium sulfate saturation of a crude sample of *N. benthamiana* plant leaves expressing said light and heavy chain, followed by thorough mixing at 4° C., followed by a second ammonium sulfate precipitation at 50% ammonium sulfate saturation to produce a 50% ammonium sulfate pellet;

b) resuspending said 50% ammonium sulfate pellet in a buffer, applying said suspension to a Protein A affinity column, and eluting said column with 50 mM sodium citrate, pH 2.5; and c) neutralizing the eluate from step (b) with 1M Tris-base to a final pH of 7.0 and subjecting said neutralized eluate to DEAE anion exchange chromatography, wherein said DEAE anion exchange chromatography step produces a purified plant-derived preparation of fully assembled Hu-E16 to a greater than 95% purity level.

3. The method of claim 2, wherein said method produces greater than 5 g of hu-E16 from 16 kg of plant material.

4. The method of claim 2, wherein said hu-E16 purified from said *N. benthamiana* plant leaves protects against infection from WNV.

5. The method of claim 2, wherein said hu-E16 purified from said *N. benthamiana* plant leaves ameliorates the symptoms of infection from WNV after infection by said virus.

6. The method of claim 1, wherein the nucleic acid sequence encoding the variable domain of the heavy chain wherein the variable domain has a sequence of SEQ ID NO: 1.

7. The method of claim 1, wherein the amino acid sequence of the variable domain of the heavy chain optimized heavy chain has a sequence of SEQ ID NO:2.

8. The method of claim 1, wherein the variable heavy chain amino acid sequence of the optimized heavy chain has a sequence of SEQ ID NO:3.

9. The method of claim 1, optimized heavy chain sequence has an amino acid sequence of SEQ ID NO:5.

10. The method of claim 1, wherein the amino acid sequence of the light chain optimized light chain has a sequence of SEQ ID NO:7.

11. A preparation of a plant-derived hu-E16 antibody produced according to the method of claim 2, said antibody comprising SEQ ID NO:5 and SEQ ID NO:7.

* * * * *